United States Patent
Burgi

(10) Patent No.: US 8,870,886 B2
(45) Date of Patent: Oct. 28, 2014

(54) STRAIGHT CUP IMPACTOR

(75) Inventor: Jonas Burgi, Moutier (CH)

(73) Assignee: Greatbatch Medical S.A., Clarence, NY (US)

(*) Notice: Subject to any disclaimer, the term of this patent is extended or adjusted under 35 U.S.C. 154(b) by 61 days.

(21) Appl. No.: 13/594,922

(22) Filed: Aug. 27, 2012

(65) Prior Publication Data

US 2013/0226186 A1 Aug. 29, 2013

Related U.S. Application Data

(60) Provisional application No. 61/527,684, filed on Aug. 26, 2011.

(51) Int. Cl.
*A61F 2/46* (2006.01)
*A61B 17/56* (2006.01)
*A61F 2/30* (2006.01)

(52) U.S. Cl.
CPC .............. *A61B 17/56* (2013.01); *A61F 2/4609* (2013.01); *A61F 2002/30471* (2013.01); *A61F 2002/30522* (2013.01); *A61F 2002/4627* (2013.01); *A61F 2002/4629* (2013.01); *A61F 2002/4681* (2013.01)
USPC .......................................................... 606/91

(58) Field of Classification Search
CPC ................ A61F 2/4609; A61F 2/4612; A61F 2002/4625; A61F 2002/4627
USPC ...................... 606/81, 91, 99, 100; 623/22.12; 81/177.2, 53.1
See application file for complete search history.

(56) References Cited

U.S. PATENT DOCUMENTS

| | | | |
|---|---|---|---|
| 1,942,422 A | | 6/1931 | Hanna |
| 2,670,881 A | * | 3/1954 | Sjoblom ...................... 222/289 |
| 2,845,805 A | * | 8/1958 | Crewe .............................. 74/169 |
| 3,290,953 A | * | 12/1966 | Ulm .............................. 74/141.5 |
| 4,305,394 A | | 12/1981 | Bertuch, Jr. |
| 4,385,529 A | * | 5/1983 | Ejiri et al. ....................... 74/535 |
| D272,648 S | | 2/1984 | Bolesky et al. |
| D273,806 S | | 5/1984 | Bolesky et al. |
| 4,475,549 A | | 10/1984 | Oh |

(Continued)

FOREIGN PATENT DOCUMENTS

EP 0470912 12/1992
EP 0535973 4/1993

(Continued)

OTHER PUBLICATIONS

European Search Report dated Nov. 19, 2012.

*Primary Examiner* — Michael T. Schaper
*Assistant Examiner* — Amy Sipp
(74) *Attorney, Agent, or Firm* — Steven W. Winn

(57) ABSTRACT

An orthopedic impactor device for positioning an orthopedic prosthetic cup implant during a hip replacement surgery is described. The impactor is designed with a "one piece" elongated body portion, having a distal prosthetic cup engagement portion which is separated from a proximal strike plate by an elongated body and handle portions. A connection rod, connectable to an orthopedic prosthetic cup, is positioned longitudinally within the through-bores of the body and handle portions. A lever arm, having a linkage member, is pivotally connected to the rod such that when the lever arm is pivoted towards the exterior surface of the annular sidewall of the handle portion, the distal end of the rod moves within the body portion.

21 Claims, 10 Drawing Sheets

(56) References Cited

U.S. PATENT DOCUMENTS

| | | | |
|---|---|---|---|
| 4,520,511 A | 6/1985 | Gianezio et al. | |
| 4,528,980 A | 7/1985 | Kenna | |
| 4,587,964 A | 5/1986 | Walker et al. | |
| 4,615,551 A * | 10/1986 | Kinaga et al. | 297/341 |
| 4,632,111 A | 12/1986 | Roche | |
| 4,716,894 A | 1/1988 | Lazzeri et al. | |
| 4,765,328 A | 8/1988 | Keller et al. | |
| 4,834,112 A * | 5/1989 | Machek et al. | 600/587 |
| 4,904,267 A | 2/1990 | Bruce et al. | |
| 4,919,679 A | 4/1990 | Averill et al. | |
| 4,921,493 A | 5/1990 | Webb, Jr. et al. | |
| 5,019,105 A | 5/1991 | Wiley | |
| 5,037,424 A | 8/1991 | Aboczsky | |
| 5,061,270 A * | 10/1991 | Aboczky | 606/91 |
| 5,062,854 A | 11/1991 | Noble et al. | |
| 5,089,003 A | 2/1992 | Fallin et al. | |
| 5,116,339 A | 5/1992 | Glock | |
| 5,124,106 A | 6/1992 | Morr et al. | |
| 5,133,766 A | 7/1992 | Halpern | |
| 5,169,399 A * | 12/1992 | Ryland et al. | 606/91 |
| 5,190,549 A * | 3/1993 | Miller et al. | 606/85 |
| 5,234,432 A | 8/1993 | Brown | |
| 5,261,915 A | 11/1993 | Durlacher et al. | |
| 5,324,293 A | 6/1994 | Rehmann | |
| 5,342,362 A | 8/1994 | Kenyon et al. | |
| 5,364,403 A | 11/1994 | Petersen et al. | |
| 5,417,696 A | 5/1995 | Kashuba et al. | |
| 5,443,471 A | 8/1995 | Swajger | |
| 5,454,815 A | 10/1995 | Geisser et al. | |
| 5,485,887 A | 1/1996 | Mandanis | |
| 5,584,837 A | 12/1996 | Petersen | |
| 5,628,752 A * | 5/1997 | Asnis et al. | 606/104 |
| 5,658,294 A | 8/1997 | Sederholm | |
| 5,665,091 A | 9/1997 | Nobel et al. | |
| 5,683,399 A | 11/1997 | Jones | |
| 5,707,374 A | 1/1998 | Schmidt | |
| 5,720,750 A | 2/1998 | Koller et al. | |
| 5,863,295 A | 1/1999 | Averill et al. | |
| 5,913,860 A | 6/1999 | Scholl | |
| 5,976,148 A | 11/1999 | Charpenet et al. | |
| 5,993,455 A | 11/1999 | Noble | |
| 6,063,124 A | 5/2000 | Amstutz | |
| 6,120,508 A | 9/2000 | Grunig et al. | |
| 6,197,065 B1 | 3/2001 | Martin et al. | |
| 6,432,141 B1 | 8/2002 | Stocks et al. | |
| 6,451,058 B2 | 9/2002 | Tuke et al. | |
| 6,626,913 B1 | 9/2003 | McKinnon et al. | |
| 6,663,636 B1 | 12/2003 | Lin | |
| 6,811,569 B1 | 11/2004 | Afriat et al. | |
| 7,192,449 B1 | 3/2007 | McQueen et al. | |
| 7,341,593 B2 | 3/2008 | Auxepaules et al. | |
| 7,396,357 B2 | 7/2008 | Tornier et al. | |
| 7,585,301 B2 | 9/2009 | Santarella et al. | |
| 7,591,821 B2 | 9/2009 | Kelman | |
| 7,604,667 B2 | 10/2009 | DeSmet et al. | |
| 7,922,726 B2 | 4/2011 | White | |
| 2001/0051830 A1 | 12/2001 | Tuke et al. | |
| 2002/0004660 A1 | 1/2002 | Henniges et al. | |
| 2002/0116007 A1 | 8/2002 | Lewis | |
| 2002/0177854 A1 | 11/2002 | Tuke et al. | |
| 2002/0193797 A1 | 12/2002 | Johnson et al. | |
| 2003/0009234 A1 | 1/2003 | Treacy et al. | |
| 2003/0050645 A1 * | 3/2003 | Parker et al. | 606/99 |
| 2003/0083668 A1 | 5/2003 | Rogers et al. | |
| 2003/0088316 A1 | 5/2003 | Ganjianpour | |
| 2003/0187512 A1 | 10/2003 | Frederick et al. | |
| 2003/0220698 A1 | 11/2003 | Mears et al. | |
| 2003/0229356 A1 | 12/2003 | Dye | |
| 2004/0215200 A1 | 10/2004 | Tornier et al. | |
| 2005/0038443 A1 | 2/2005 | Hedley et al. | |
| 2005/0075736 A1 | 4/2005 | Collazo | |
| 2005/0137603 A1 | 6/2005 | Belew et al. | |
| 2005/0171548 A1 | 8/2005 | Kelman | |
| 2005/0222572 A1 | 10/2005 | Chana | |
| 2005/0228395 A1 | 10/2005 | Auxepaules et al. | |
| 2005/0234462 A1 | 10/2005 | Hershberger | |
| 2005/0246031 A1 | 11/2005 | Frederick et al. | |
| 2006/0052780 A1 | 3/2006 | Errico et al. | |
| 2006/0149285 A1 | 7/2006 | Burgi et al. | |
| 2007/0156155 A1 | 7/2007 | Parker | |
| 2007/0167952 A1 | 7/2007 | Burgi et al. | |
| 2007/0270783 A1 | 11/2007 | Zumsteg et al. | |
| 2007/0288096 A1 | 12/2007 | Surma | |
| 2007/0293869 A1 | 12/2007 | Conte et al. | |
| 2008/0004628 A1 | 1/2008 | White | |
| 2008/0021481 A1 | 1/2008 | Burgi | |
| 2008/0033444 A1 | 2/2008 | Bastian et al. | |
| 2008/0077249 A1 * | 3/2008 | Gradel | 623/22.15 |
| 2008/0146969 A1 | 6/2008 | Kurtz | |
| 2008/0154261 A1 | 6/2008 | Burgi | |
| 2008/0172061 A1 * | 7/2008 | Ragbir | 606/99 |
| 2008/0228191 A1 * | 9/2008 | Downs et al. | 606/90 |
| 2008/0243127 A1 | 10/2008 | Lang et al. | |
| 2008/0255565 A1 | 10/2008 | Fletcher | |
| 2008/0255568 A1 * | 10/2008 | Tornier et al. | 606/91 |
| 2008/0262503 A1 | 10/2008 | Muller | |
| 2008/0275450 A1 | 11/2008 | Myers et al. | |
| 2009/0112214 A1 | 4/2009 | Philippon et al. | |
| 2009/0182334 A1 | 7/2009 | Brehm | |
| 2009/0192515 A1 * | 7/2009 | Lechot et al. | 606/91 |
| 2009/0240256 A1 | 9/2009 | Smith | |
| 2009/0281545 A1 | 11/2009 | Stubbs | |
| 2013/0018382 A1 * | 1/2013 | Jones et al. | 606/99 |

FOREIGN PATENT DOCUMENTS

| | | |
|---|---|---|
| EP | 357302 | 7/1994 |
| EP | 638299 | 2/1995 |
| EP | 1308140 | 5/2003 |
| EP | 1190687 | 7/2004 |
| EP | 1447058 | 8/2004 |
| EP | 2345392 | 7/2011 |
| FR | 2900328 | 11/2007 |
| WO | 0012832 | 3/2000 |
| WO | 0106964 | 2/2001 |
| WO | 2005044153 | 5/2005 |
| WO | 2006061708 | 6/2006 |
| WO | 2007098549 | 9/2007 |
| WO | 2008128282 | 10/2008 |

* cited by examiner

STRAIGHT CUP IMPACTOR

CROSS-REFERENCE TO RELATED APPLICATIONS

This application claims priority from U.S. Provisional Patent Application Ser. No. 61/527,684, filed Aug. 26, 2011.

FIELD OF THE INVENTION

The invention relates to surgical tools for aiding a surgeon installing an orthopedic prosthesis. More specifically, the invention relates to an orthopedic cup impactor for positioning an acetabular cup prosthesis within the body.

BACKGROUND OF THE INVENTION

A total hip replacement is a reconstructive surgical procedure typically performed by an orthopedic surgeon. A total hip replacement involves placement of an acetabular cup within a patient's acetabular socket and replacement of the patient's femoral neck with a prosthesis which terminates in a ball specifically designed to be positioned in the acetabular cup. Other surgical procedures may require the application of an acetabular cup or other device applied to a patient.

For example, during such acetabular cup procedures, the patient's acetabular socket is reamed out by the surgeon so as to create an enlarged recess to receive the acetabular cup. After the acetabular socket has been reamed, the cup is inserted into the recess and adjusted as necessary to the proper angular orientation. Once deployed, the cup provides a new socket and lining for the patient's acetabulum.

Insertion and placement of the cup by the surgeon is effected either by hand or use of a hand tool that grips the cup. Once the cup is properly positioned in the acetabulum, the cup can be fixed in the desired location by various means such as bone screws, medically acceptable adhesives, or combinations thereof. In many instances, the fixation means include passing bone screws through the cup and into pre-drilled screw holes in the pelvic bone. The bone screws, which are optional, serve to hold the acetabular cup in the acetabulum until bone ingrowth provides permanent fixation.

In one acceptable medical method, the cup is properly positioned in the acetabulum by implantation. One conventional implantation method is, after obtaining proper alignment, to impact an acetabular cup into place. While impacting the acetabular cup, the surgeon listens for a change in pitch as the cup seats down. The surgeon then probes screw holes to determine if a gap between the cup and the bone is present. If a gap is present, the surgeon further impacts the cup into the acetabulum.

FIGS. 1, 2 and 2A illustrate a conventional spindle-type orthopedic surgical impactor 10. As shown, this prior art impactor 10 has a strike plate 12 that is integrally connected to a proximal end 16 of the impactor body 14. Extending from the strike plate 12 and positioned over a proximal area of the body portion 14 is a fixed handle 18. The fixed handle 18 has a length that allows a surgeon to hold the impactor 10, in one embodiment with one hand, and in an alternative embodiment with two hands. Whatever the fixed handle's 18 length, extending there from on the body 14, is an impactor thread section 20. At the body portion's distal end 22 is a tool thread section 24.

The tool thread section 24 threadingly interconnects to a surgical implant device (a.k.a., medical attachment) 26, for example, and not limited to, an acetabular cup, through a threaded aperture 28 (FIG. 2). That means the implant device 26 is directly connected to the body 14 and the strike plate 12. To ensure the surgical implant device 26 is properly secured to the tool thread section 24, the prior art device 10 uses a rotate handle device 30 (FIG. 2A).

The rotate handle 30 is positioned in the spacing between the tool thread section 24 and the impactor thread section 20. At its proximal end, the rotate handle device 30 has a rotating threaded section 32 and at its distal end, an implant support 34. The rotating threaded section 32 has threads that mate with the impactor thread section 20. When the rotating threaded section 32 is rotated clockwise (illustrated by arrow 36 at FIG. 1), (a) the rotating threaded section 32 pushes (illustrated by arrow 38) the rotate handle 30 and the implant support surface 34 toward the surgical implant device's interior surface 40 (FIG. 2); and (b) simultaneously, the rotating threaded section 32, through a conventional lock-nut structure, rotates the surgical implant device 26 counter-clockwise (arrow 42 at FIG. 1). This movement results in the surgical implant 26 being pushed toward the implant support 34. Collectively, the clockwise rotating threaded section 32 is designed to securely position the surgical implant 26 against the implant support 34 to inhibit dislodging of the surgical implant device 26 from the spindle-type tool holder 10 when the surgeon impacts the tool holder.

However, when the surgeon impacts the strike plate 12 there is a possibility that the surgical implant 26 can disconnect from the impactor 10. This could occur when the threaded section 24 or the implant's 26 corresponding threaded section 28 is damaged from the impaction force. Accordingly, what is needed is a firm fixation of the surgical implant 26 during impaction that provides minimal damage to the implant's 26 threads 28. That desired product is achieved with the present invention.

SUMMARY OF THE INVENTION

The cup impactor of the present invention comprises an elongated body with respective distal and proximal ends. The elongated body is constructed with a strike plate residing at the body's proximal end, a handle portion, and an impactor cup engagement portion located at the body's opposing distal end. The elongated body is constructed of a one-piece design. The elongated body is designed such that the strike plate fluidly extends from the proximal end portion to the handle portion through a body length portion and to the impactor cup engagement portion at the distal end portion.

A connection rod, having respective proximal and distal rod ends, is positioned within an elongated through-bore of the body and housing portions. The distal end of the connection rod is constructed with a threaded end that is designed to threadably attach to a threaded aperture of a prosthetic orthopedic cup. The proximal end portion of the connection rod resides within the handle through-bore such that the rod's proximal end does not contact the inside wall surface residing at the proximal end of the impactor at the handle.

Therefore, because the proximal end of the connection rod is prevented from contacting the inner surface of the proximal end of the cavity of the handle, the possibility that impaction forces are transferred to the surgical implant through the connection rod, is reduced. As a result, the possibility of causing damage to the cup implant, particularly the prosthetic cup's connection mechanism, is reduced.

In an embodiment of the impactor of the present invention, the proximal end portion is pivotably connected to a lever arm subassembly comprising a lever arm and linkage member. This lever arm subassembly actuates movement of the connection rod and thus movement of the prosthetic cup. The lever arm subassembly is designed such that when the lever arm is moved in a pivotable manner in a downward direction, i.e., closer to the external surface of the handle's annular sidewall, the connection rod is retracted into the through-bore of the body. Since the distal end of the connection rod is preferably connected to the prosthetic cup, retraction of the rod within the body pulls the implant cup in a proximal direction, closer to the cup engaging portion of the impactor. Likewise, when the lever arm is pivoted away from the external surface of the annular sidewall of the handle, the connection rod and, therefore, the prosthetic cup, move distally away from the distal end of the impactor.

In a further embodiment of the impactor of the present invention, a releasable ratchet locking mechanism is provided. The locking mechanism enables the prosthetic cup to be locked in a multitude of positions with respect to the impactor. The locking mechanism release lever further allows for quick release and removal of the prosthetic cup from the impactor.

In yet another embodiment of the impactor of the present invention, the one-piece construction of the impactor body portion of the impactor minimizes the possibility that the associated components of the impactor are misplaced. The impactor is constructed such that its components are either connected to or contained within the elongated body or handle portions, thereby preventing displacement of the components from the impactor.

BRIEF DESCRIPTION OF THE DRAWINGS

FIG. 2A illustrates the prior art handle device 30 of FIG. 1.

DETAILED DESCRIPTION OF THE INVENTION

Figure 1:
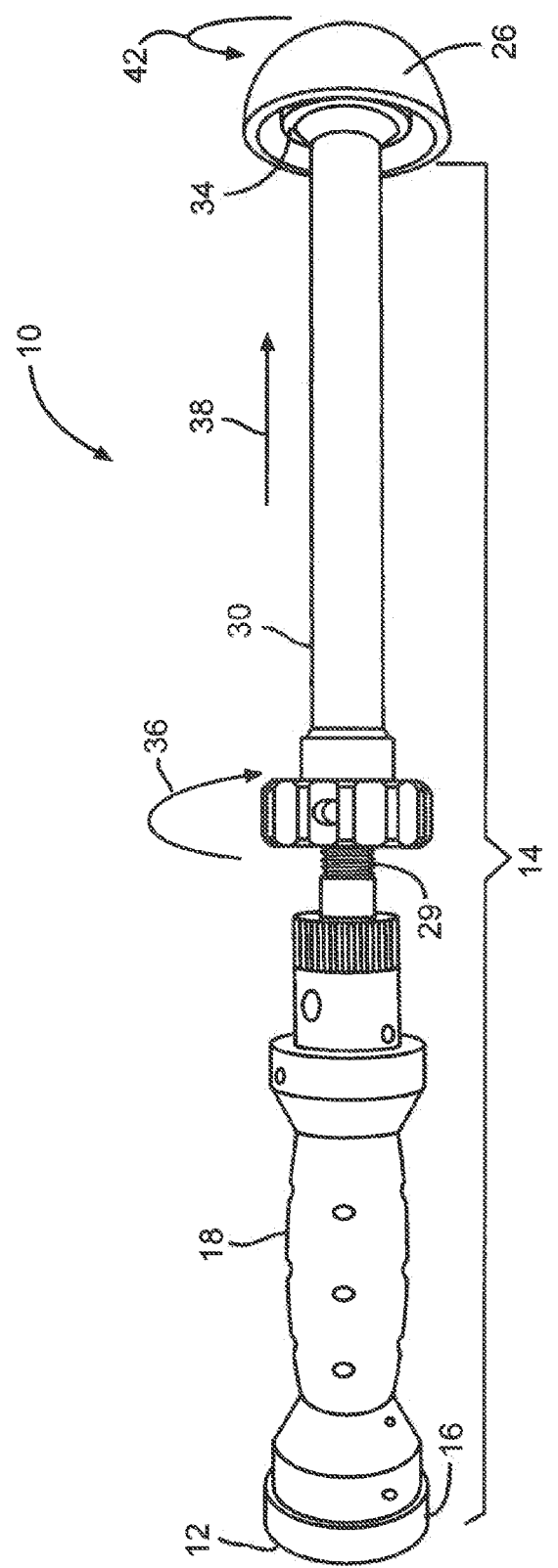
FIG. 1 illustrates an embodiment of a prior art orthopedic impactor.
Figure 2:
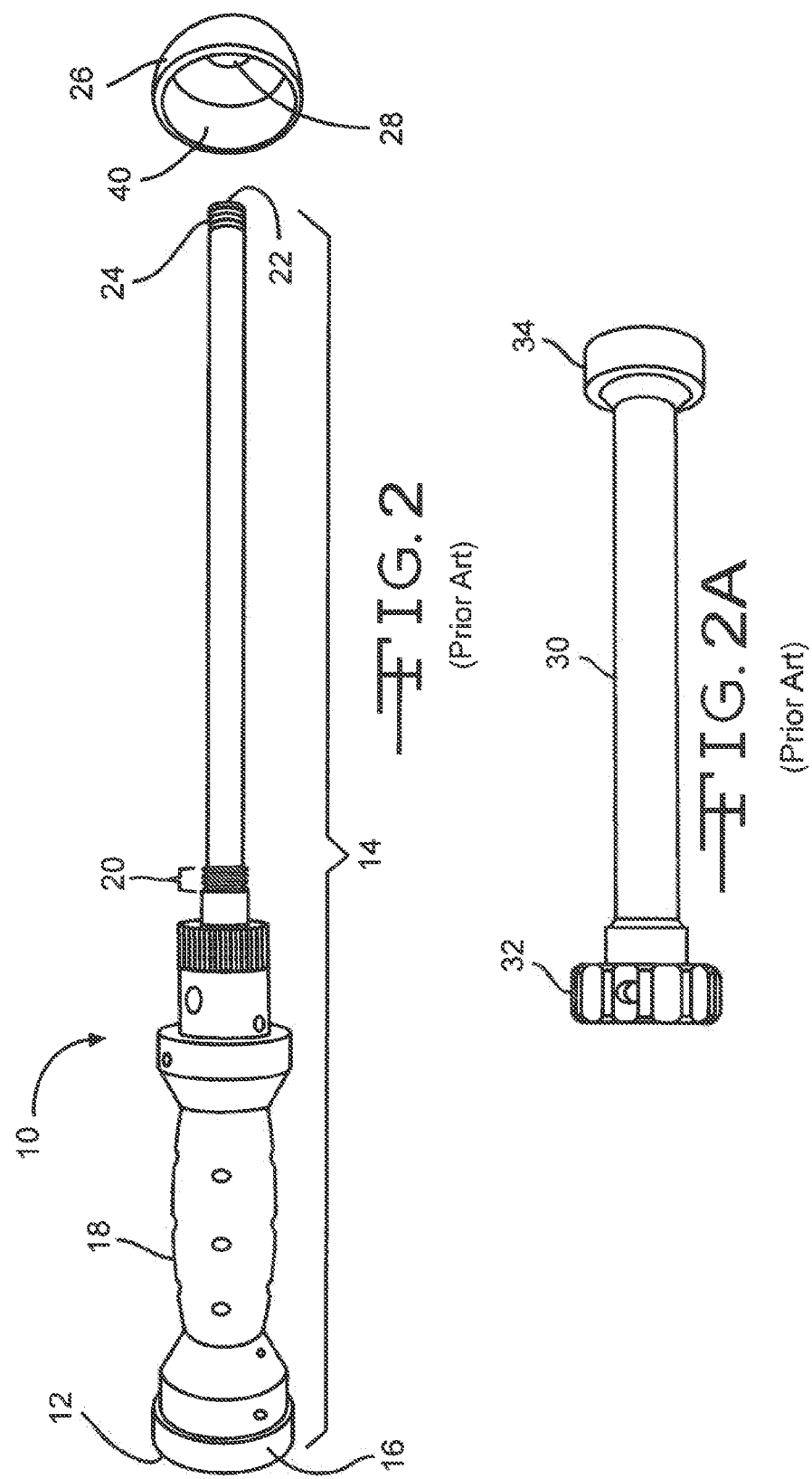
FIG. 2 shows the handle 18 and connected body portion 14 of the prior art impactor shown in FIG. 1.
Figure 3:
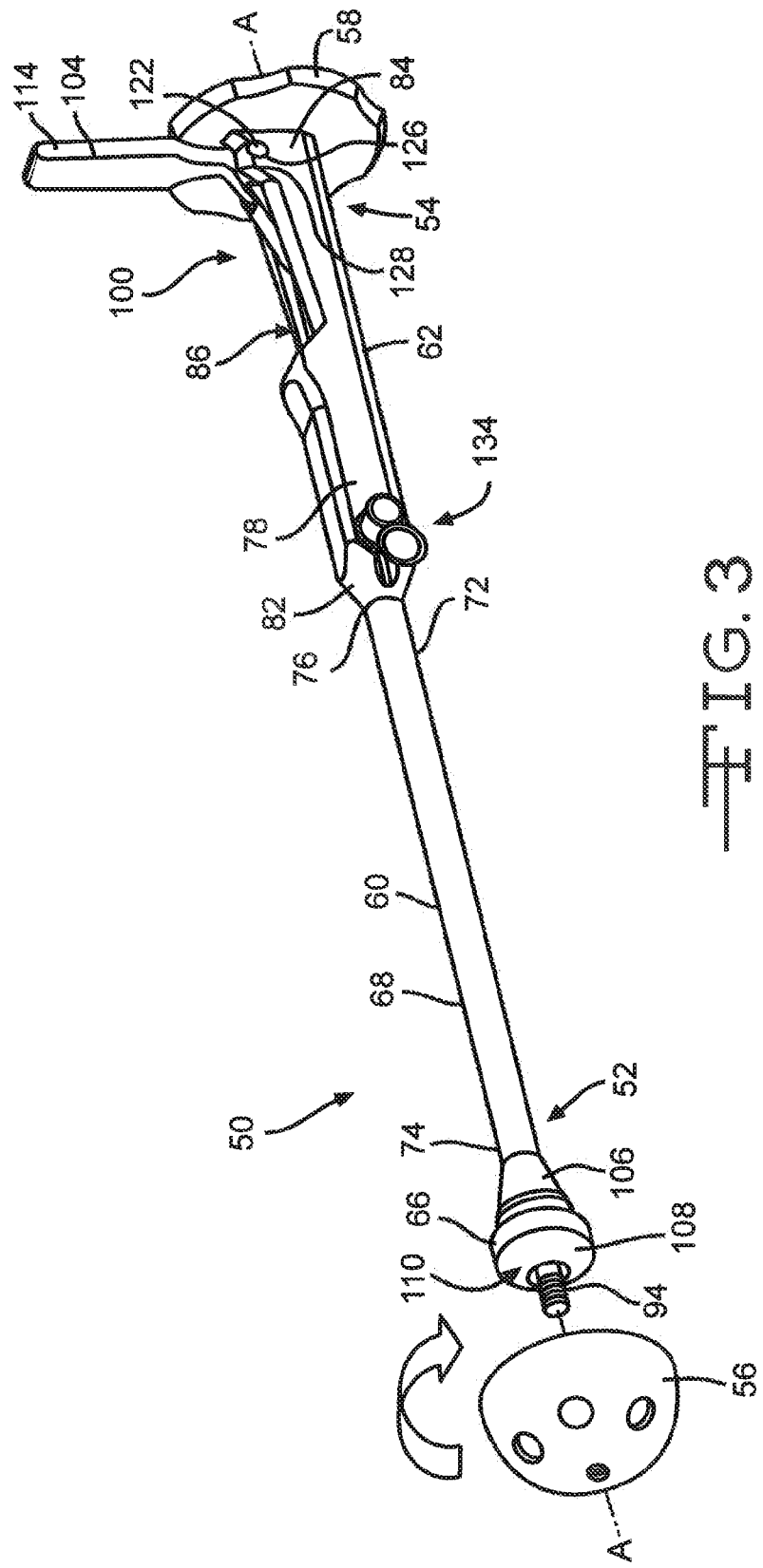
FIG. 3 illustrates a perspective view of the spindle-type orthopedic impactor of the present invention.

Now turning to the figures, FIGS. 3-7 illustrate a spindle-type orthopedic impactor 50 of the present invention. As shown in FIG. 3, the orthopedic impactor 50 comprises a distal end portion 52 spaced from a proximal end portion 54 with a length portion residing therebetween. An orthopedic prosthetic cup 56 is designed to be positioned at the distal end of the impactor 50 and a strike plate 58 resides at the proximal end of the impactor 50.

More specifically as illustrated in FIGS. 3-7, the impactor 50 of the present invention comprises an elongated body portion 60 and a handle portion 62. The handle portion 62 resides between the body 60 and the strike plate 58. A connection rod 64 is positioned within the body and handle portions 60 and 62, respectively. As shown, the body portion 60 and handle portion 62 extend lengthwise along longitudinal axis A-A. In a preferred embodiment, the body portion 60 and handle portion 62 are of a "one-piece" construction in that the strike plate 58, located at the proximal end of the impactor 50, and the elongated body are fluidly connected together in one-piece. A prosthetic cup engagement portion 66, located at the distal end of the impactor 50 is threadingly mated to the distal end of the body portion 60.

The elongated body portion 60 is constructed with a curved body sidewall 68. More preferably, the elongated body portion 60 is constructed with an annular body sidewall 68 with an outer diameter ranging from about 1 cm to about 5 cm. Although it is preferred that the elongated body is constructed with a sidewall 68 having a circular cross-section, the body 60 may be constructed of a multitude of cross-sectional shapes that include, but are not limited to, a rectangle, a square, a triangle, a hexagon, or an oval.

The elongated body portion 60 has a length that ranges from about 5 cm to about 50 cm and more preferably from about 10 cm to about 25 cm. The body portion 60 may be constructed of either a polymer, metallic, or composite material. Specifically, the body portion 60 may be constructed from polymers comprising polyether ether ketone (PEEK), acryloyl b-alanine (ABA), acryloyl b-alanine tri-block copolymers and the like. In addition, the body portion may be constructed from metals comprising aluminum, stainless steel, cobalt nickel alloys, highly alloyed ferritic stainless steel containing molybdenum and chromium, and nickel chromium- and molybdenum-containing alloys, and the like. Furthermore, the body portion 60 may be constructed from composite materials such as carbon fiber or combinations of polymeric and metallic materials.

Figure 4:
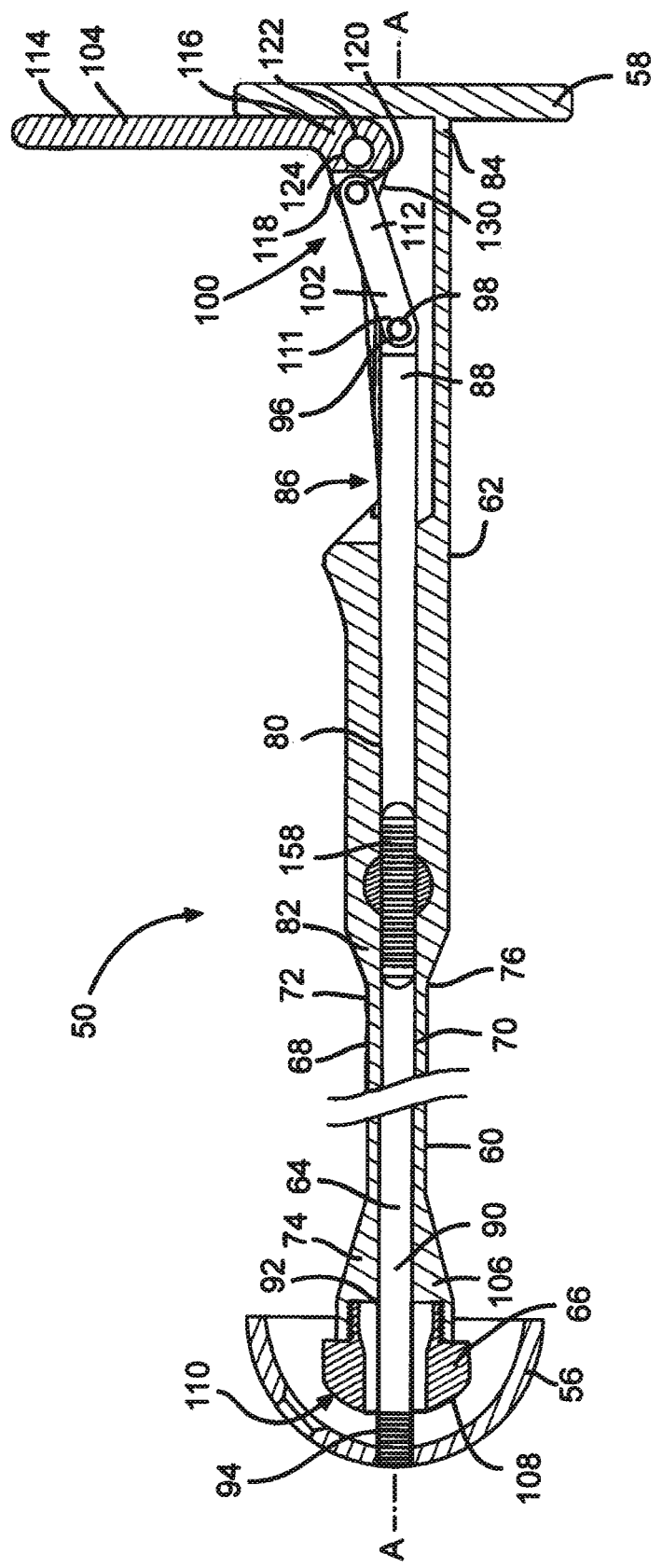
FIG. 4 is a cross-sectional view of an embodiment of the components comprising the orthopedic impactor of the present invention.
Figure 6:
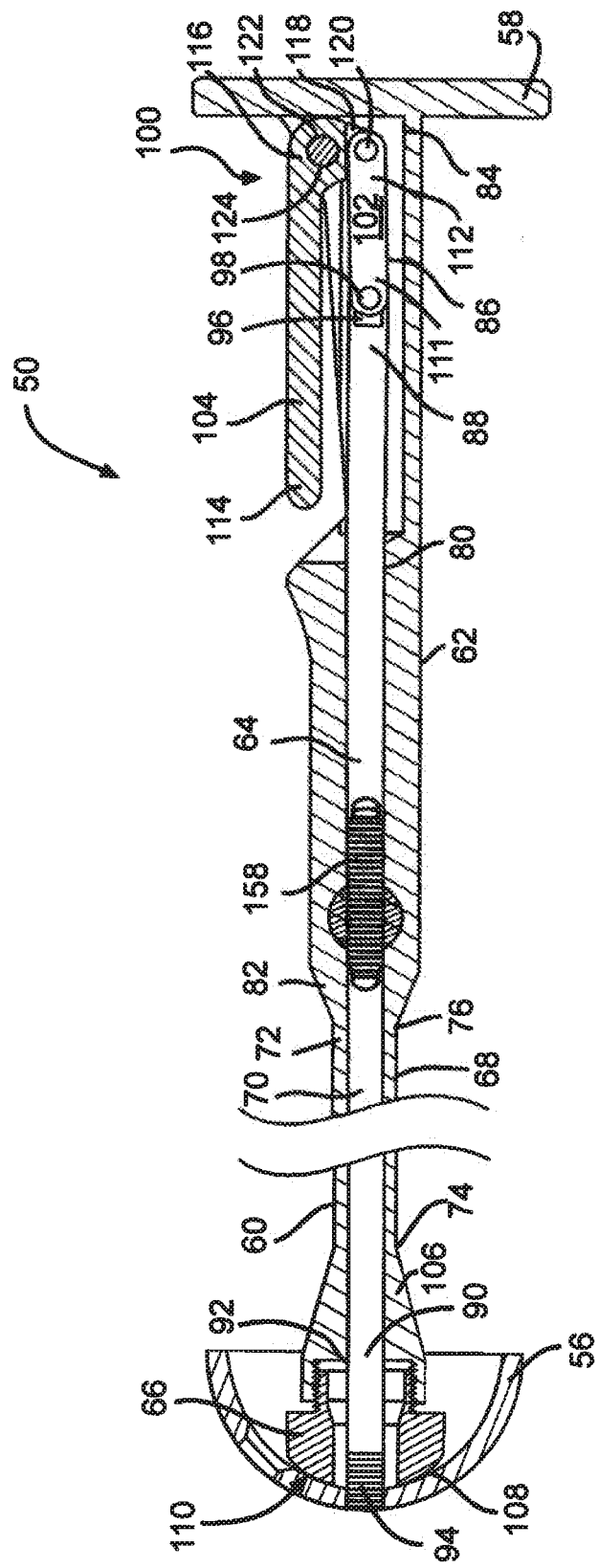
FIG. 6 illustrates a cross-sectional view of the orthopedic prosthetic cup attached to the impactor shown in FIG. 5.
Figure 7:
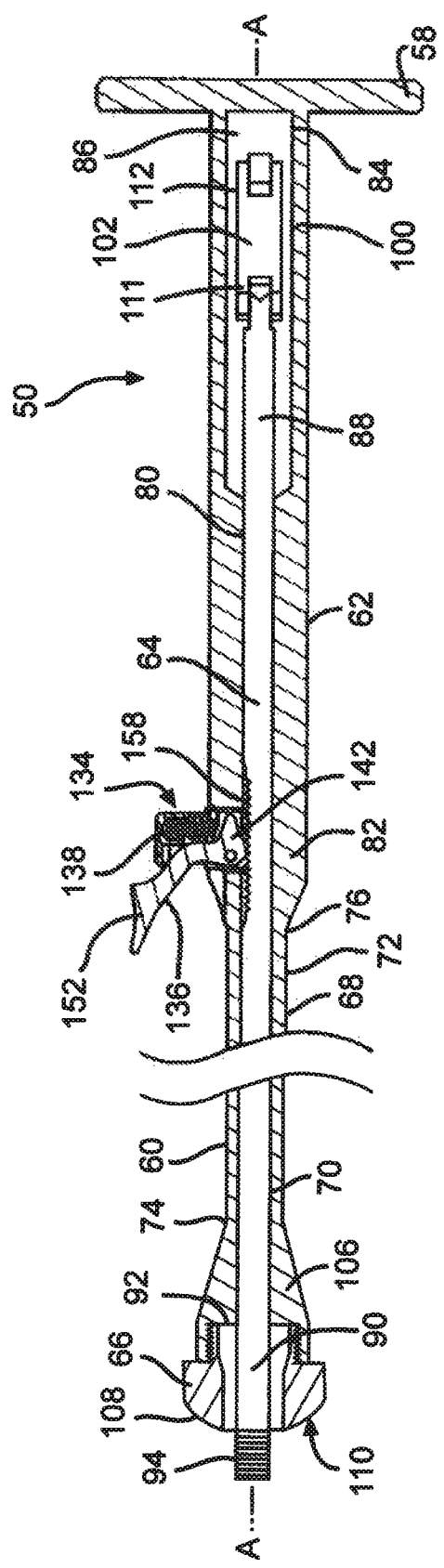
FIG. 7 is a cross-sectional view of an embodiment of locking mechanism of the orthopedic impactor.

As shown in FIGS. 4, 6 and 7, the elongated body portion has an elongated body through-bore 70 that extends from a body proximal end portion 72 to a distal end 74 of the body 60 along longitudinal axis A-A. In a preferred embodiment, the body through-bore 70 has a cylindrical shape with a generally circular cross-section providing a cavity diameter ranging from about 0.5 cm to about 4 cm. The through-bore 70 may be constructed of a multitude of cross-sectional shapes that include, but are not limited to, a rectangle, a square, a triangle, a hexagon, an oval, or the like.

Extending proximally from the elongated body portion 60 is the handle portion 62 of the impactor 50. As shown in FIGS. 3-7, the handle portion 62 is positioned between a proximal end 76 of the body 60 and the strike plate 58. More specifically, the handle portion 62 is positioned such that it fluidly transitions between the elongated body portion 60 and the strike plate 58. In a preferred embodiment, the handle portion 62 has a generally tubular form providing an annular handle sidewall 78. Although it is preferred that the handle portion is constructed with a rectangular cross-section, the handle 62 may be constructed of a multitude of cross-sectional shapes that include, but are not limited to, a curve, a circle, a square, a triangle, a hexagon, or an oval.

The handle portion 62 preferably has an inner handle diameter ranging from about 1 cm to about 3 cm. A handle through-bore 80 extends longitudinally along axis A-A from a handle distal end 82 to a handle proximal end 84. The handle through-bore 80 is aligned with the elongated body through-bore 70 along longitudinal axis A-A.

The handle portion 62 has a length that ranges from about 5 cm to about 50 cm and more preferably from about 10 cm to about 25 cm. Like the elongated body portion 60, the handle portion 62 may be constructed of either a polymer or metallic material. The handle portion 62 may be constructed from polymers comprising polyether ether ketone (PEEK), acryloyl b-alanine (ABA), acryloyl b-alanine tri-block copolymers and the like. In addition, the handle portion may be constructed from metals comprising aluminum, stainless steel, cobalt nickel alloys, highly alloyed ferritic stainless steel containing molybdenum and chromium, and nickel chromium- and molybdenum-containing alloys, and the like.

In an embodiment, the proximal end 84 of the handle portion 62 comprises a cavity 86. The cavity 86 extends completely through the thickness of the annular sidewall 78 of the handle portion 62, but only for a portion of the annular extent of the sidewall 78. This structure provides the cavity 86 having a channel shape that extends from the proximal end 84 of the handle 62 to a point, distal of the handle portion's proximal end 84. In a preferred embodiment, the cavity 86 has a length ranging from about 5 cm to about 15 cm and a depth and width that spans the distance between opposed inner surfaces of the annular handle sidewall 78.

Positioned within the elongated body and handle portions 60, 62 is the connection rod 64. The rod 64 is constructed such that it is in a slidable relationship within the through-bores of the elongated body and handle portions 60, 62. The connection rod 64 has a rod proximal end portion 88 spaced apart from a rod distal end portion 90 with a rod length residing therebetween. The connection rod 64 is preferably positioned within the through-bore 70 of the body 60 such that its proximal end portion 88 extends past the proximal end 76 of the body 60 and resides within the handle portion 62. More specifically, the proximal end portion 88 of the connection rod 64 extends within the handle portion 62 to a point distal of the handle's proximal end. A gap resides between the proximal end of the connection rod 64 and the proximal end of the handle portion 62. When the connection rod 64 is positioned within the impactor 50, a portion of the proximal end of the connection rod 64 is viewable through the cavity 86 of the handle 62. At the opposite end of the impactor 50, the distal end portion 90 of the rod 64 protrudes through a distal end 92 of the elongated body 60.

The connection rod 64 has a length ranging from about 5 cm to about 50 cm and more preferably from about 10 cm to about 20 cm. The connection rod 64 has a curved cross-section and more preferably, a circular cross-section. In a preferred embodiment, the rod 64 has a cross-sectional diameter ranging from about 0.5 cm to about 4 cm. Similarly to the body portion 60, as previously described, the rod 64 may be constructed of a multitude of cross-sectional shapes that include but are not limited to, a rectangle, a square, a triangle, a hexagon, or an oval. In a preferred embodiment, the connection rod 64 may be constructed from metals comprising aluminum, stainless steel, cobalt nickel alloys, highly alloyed ferritic stainless steel containing molybdenum and chromium, and nickel-, chromium- and molybdenum-containing alloys, and the like. Alternatively, the connection rod 64 may be constructed from polymers comprising polyether ether ketone (PEEK), acryloyl b-alanine (ABA), acryloyl b-alanine tri-block copolymers and the like. In addition, the connection rod 64 may be constructed from composite materials such as carbon fiber or combinations of polymeric and metallic materials.

In a preferred embodiment, a distal end 94 of the rod 64 has a threaded end that is designed to engage with a threaded receiving end of the prosthetic cup 56. As shown in FIGS. 4 and 6, a connection rod through-bore opening 96 is positioned at the opposite, proximal end 88 of the rod 64. The rod through-bore opening 96 extends through the diameter of the rod, perpendicular to longitudinal axis A-A. The connection rod through-bore 96 allows for the placement of a linkage member pin 98 that is designed to connect the proximal end 88 of the rod 64 to a lever arm sub-assembly 100. Specifically, the connection rod through-bore 96 allows for the placement of the linkage member pin 98 that connects to a linkage member 102 which in turn is connected to a lever arm 104. The pin is placed through the opening such that its opposing ends are in a perpendicular relationship to the longitudinal length of the rod 64. As will be discussed in more detail, this lever arm sub-assembly 100 feature of the impactor 50 enables controlled movement of the rod 64 and cup 56.

As illustrated in FIGS. 3, 4, 6 and 7, the prosthetic cup engagement portion 66 resides at the distal end 92 of the elongated body 60. The prosthetic cup engagement portion 66 is threadingly mated to a frusto-conical portion 106 at the distal end of the elongated body 60. The cap engagement portion 66 thereby provides a relatively large surface area end cap portion 108. As shown, the frusto-conical portion 106 resides at the distal end 92 of the body 60 and has a wider diameter than the diameter of the body length portion. In a preferred embodiment, the end cap 108 has a curved outer surface 110. These features of the cup engagement portion 66 are designed to contact the contoured inner surface of the prosthetic cup 56. Furthermore, the wider outer surface of the end cap 108 provides an increased surface area for a prosthetic cup to seat against during the impaction process. The greater surface area provided by the outer surface of the end cap portion 108 distributes the impaction force over a wider contact interface, therefore minimizing stress risers at the impactor 50 to prosthetic cup 56 connection point.

The strike plate 58 resides at the opposite, proximal end of the handle portion 62. The strike plate 58 is designed with a strike plate diameter that is wider than the outer diameter of the handle 62. In a preferred embodiment, the diameter of the strike plate 58 ranges from about 2 cm to about 10 cm. As illustrated, the strike plate 58 is fluidly attached to the proximal end of the handle 62.

As shown in FIGS. 3-7, the lever arm subassembly 100 is pivotally connected to the proximal end 88 of the connection rod 64. As previously mentioned, the lever arm sub-assembly 100 comprises the lever arm 104 and the linkage member 102, having a linkage member first end 110 spaced from a linkage member second end 112. As shown in FIGS. 3-7, the lever arm 104 comprises a lever portion 114, an intermediate arm portion 116 and an end arm portion 118. In a preferred embodiment, the first end 110 of the linkage member 102 is pivotally connected to the proximal end 88 of the connection rod 64. The second end 112 of the linkage member 102 is pivotally connected to the end arm portion 118 of the lever arm 104. More specifically, the second end 112 of the linkage member 102 is pivotally connected to a lever arm protrusion 130 that extends from the distal end of the lever arm 104. A distal end lever arm through-bore 132 extends perpendicularly through the protrusion 130 of the lever arm 104. A linkage member pivot pin 120 is placed through each of the connections, connecting the linkage member 102 to the proximal end 88 of the connection rod 64 and the end arm portion 118.

As illustrated in FIGS. 3-6, a connection pin 122 connects the intermediate arm portion 116 to the proximal end portion 84 of the handle portion 62. In a preferred embodiment, the connection pin 122 is positioned through a lever arm through-bore 124 and a handle through-bore 126 pivotably connecting the lever arm 104 therewithin. The connection pin 122 provides a pivotable connection between the lever arm 104, more specifically the intermediate arm portion 116, to the annular sidewall 78 of the handle portion 62.

The lever arm connection pin 122 extends perpendicularly through the lever arm through-bore 124 and connects with a corresponding lever arm support portion 128 (FIG. 5) positioned at the proximal end of the outer surface of the handle 62. In a preferred embodiment, two opposing lever arm supports 128 may be positioned across from the cavity opening 86. The intermediate portion 116 of the lever arm 104 is pivotably positioned therebetween.

The lever arm subassembly 100 is designed such that when the lever arm 104 is moved in a pivotable manner in a downward direction, towards the exterior surface of the handle portion 62, the end 118 of the lever arm pulls the proximal end of the connection rod 64 towards the proximal end 84 of the handle portion 62. More specifically, when the lever arm 104 is moved in a pivotable manner in a downward direction, the first end 111 of the linkage member 102, which is connected to the proximal end of the connection rod 64, is moved in a proximal direction to the proximal end 84 of the handle portion 62, thereby pulling the proximal end of the connection rod 64 towards the proximal end 84 of the handle portion 62. As a result, the distal end 94 of the rod 64 is retracted within the body portion 60 of the impactor 50.

Figure 5:
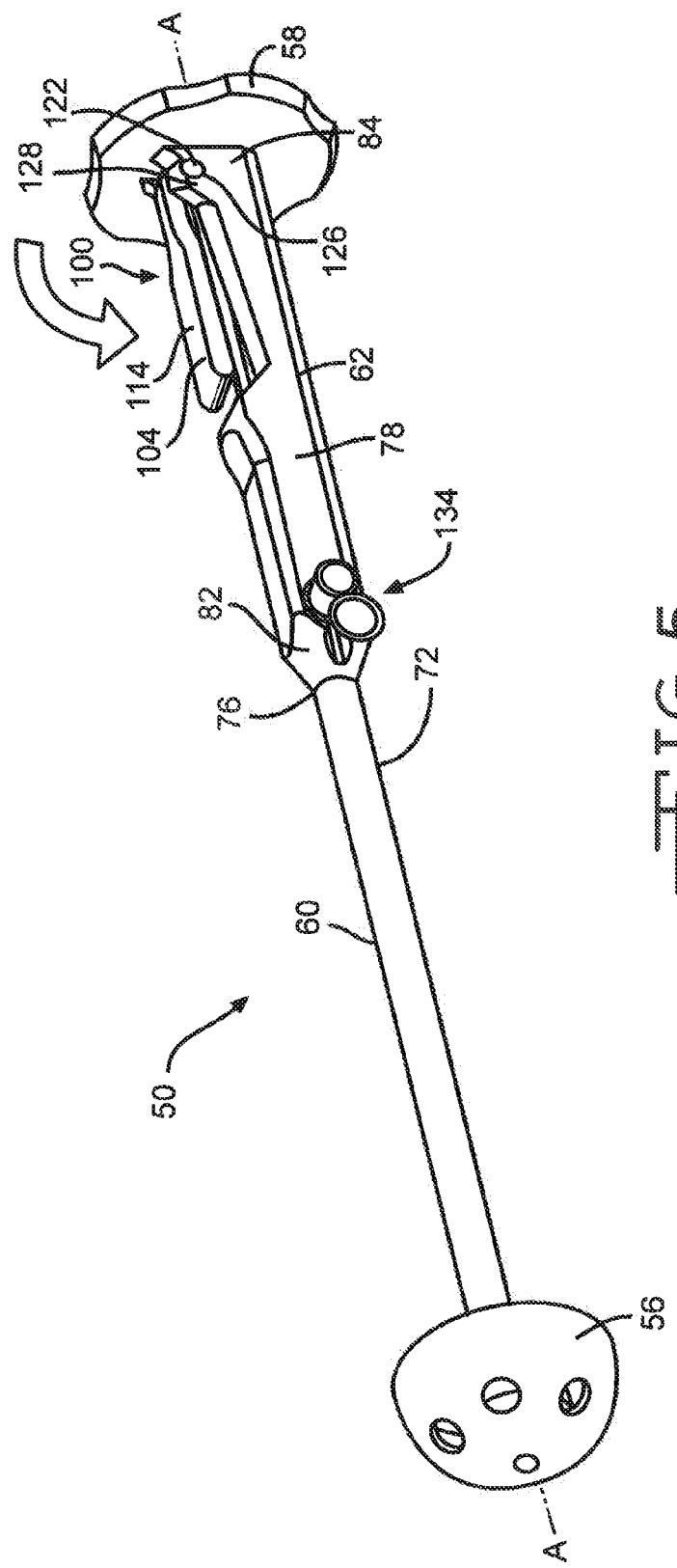
FIG. 5 illustrates a perspective view of an embodiment of an orthopedic prosthetic cup attached to the impactor shown in FIG. 3.

Therefore, when a prosthetic cup 56 is attached to the distal end 94 of the connection rod 64, proximal movement of the rod 64 pulls the cup 56 closer to the distal end of the elongated body 60 as shown in FIGS. 5 and 6. More specifically, the large end cap portion 108 providing a curved outer surface of the prosthetic cup engagement portion 66 contacts the inside surface of the prosthetic cup 56 and provides a secure fitting therebetween. In addition, the outer surface of the end cap 108 provides a larger surface area that distributes the impaction force. In a preferred embodiment, the prosthetic cup 56 is secured to the distal end of the impactor 50 through clockwise rotation of the strike plate 58 while a physician holds the prosthetic cup 56 steady in his hand. Accordingly, the impactor 50 is detached from the prosthetic cup through counterclockwise rotation of the strike plate 58 with the prosthetic cup 56 being held steady.

Figure 8:
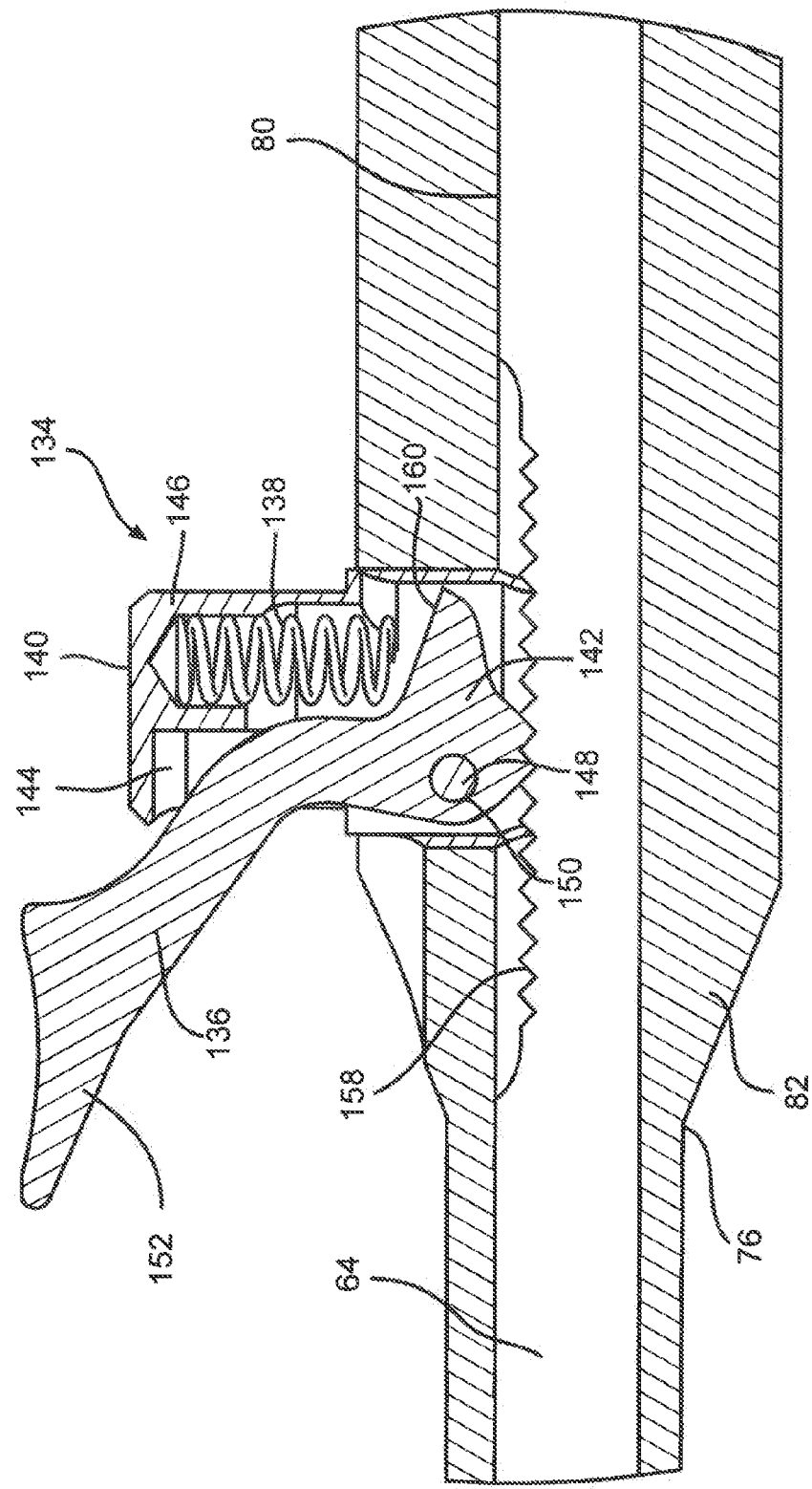
FIG. 8 illustrates a magnified cross-sectional view of an embodiment of the impactor locking mechanism.
Figure 9:
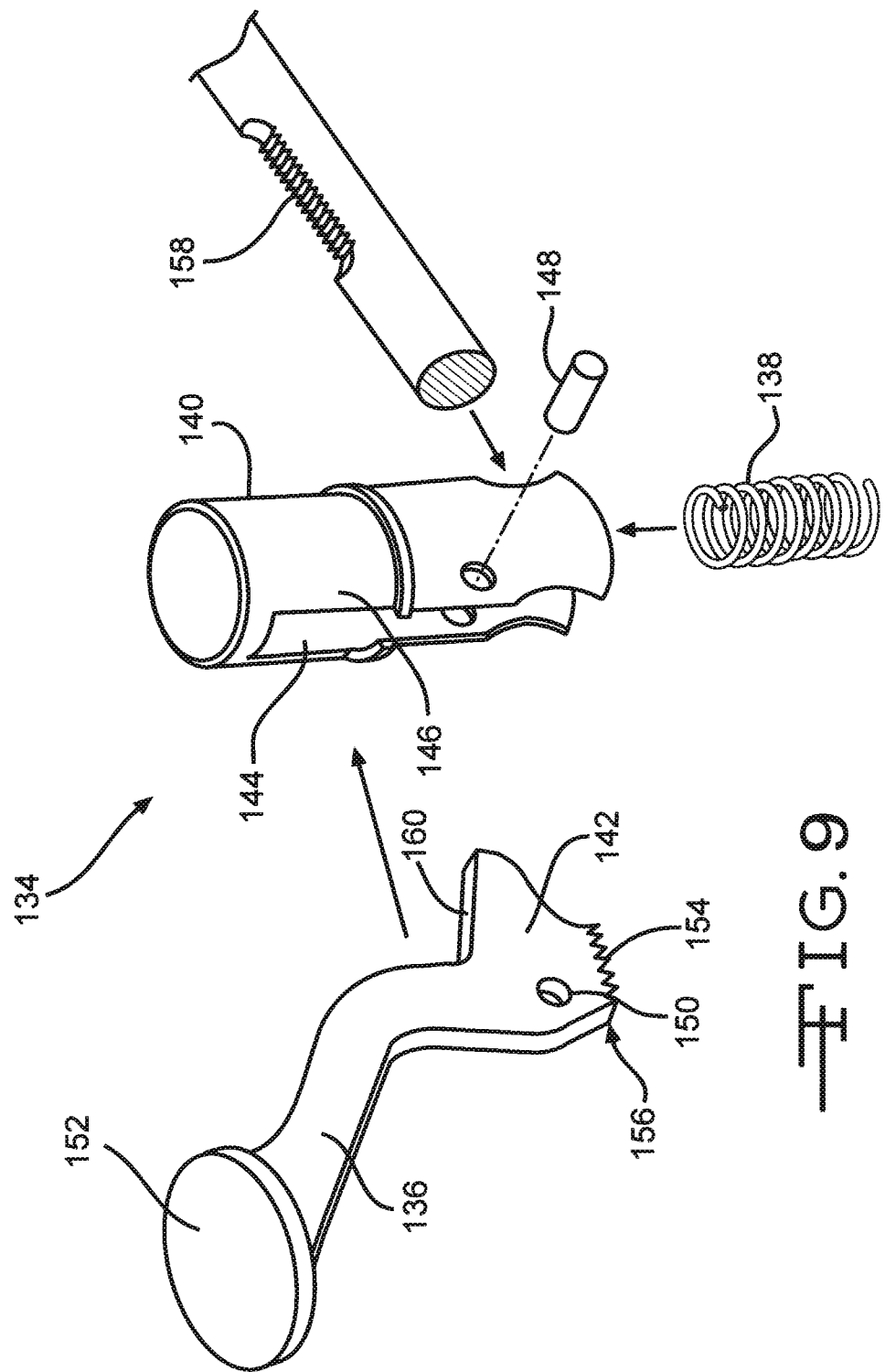
FIG. 9 shows an exploded view of the components comprising the impactor locking mechanism.

As shown in FIGS. 7, 8 and 9, a ratchet mechanism 134 is provided at the proximal end of the housing portion 62. The ratchet mechanism 134 comprises a rocker arm 136, a bias member 138, for example a coil spring, and a ratchet mechanism housing 140. In a preferred embodiment, a distal end 142 of the rocker arm 136 is positioned through an opening 144 of a sidewall 146 of the housing 140. An opposite proximal end rocker portion 152 extends outside of the ratchet mechanism housing 140. As shown in FIG. 8, the rocker arm 136 is pivotally attached to the sidewall 78 of the handle portion 62 of the impactor 50 such that the distal arm portion 142 of the rocker arm 136 is capable of penetrating within the through-bore of the handle 62.

As shown, a rocker pivot pin 148 resides through a rocker arm through-bore 150 and through the sidewall 146 of the ratchet housing 140 such that the rocker arm 136 is capable of pivoting about the pin 148. Therefore, when the proximal end 152 of the rocker arm 136 is moved in a downward direction, toward the outer surface of the housing 62, the opposite distal end 142 of the rocker arm 136 moves in an opposite upward direction, thereby disengaging the rocker teeth 154 from the connection teeth 158 (FIGS. 4 and 6 to 8).

As shown in FIGS. 8 and 9, the distal end of the rocker arm 136 comprises a series of rocker teeth 154 that protrude from an end surface 156 of the distal end portion of the rocker arm 136. The rocker arm teeth 154 are designed to engage with a series of corresponding connection rod teeth 158 as shown in the enlarged view of FIG. 8. The series of connection rod teeth 158 are formed along the exterior surface of the connection rod 64 and designed such that the individual teeth 158 protrude outwardly from the rod's surface.

The bias member 138 is positioned within the rocker mechanism housing 140. As shown in FIGS. 7 and 8, the bias member is positioned between a ledge 160 of the distal portion 142 of the rocker arm 136 and the upper sidewall of the ratchet mechanism housing 140, thereby providing a downward force that engages the teeth of the respective rocker arm and connection rod 64 therewithin. The downward force exerted by the bias member 138 within the mechanism, forces the ratchet teeth 154 and connection rod teeth 158 to become entrapped therewithin, thus preventing sliding movement of the connection rod 64.

Figure 10:
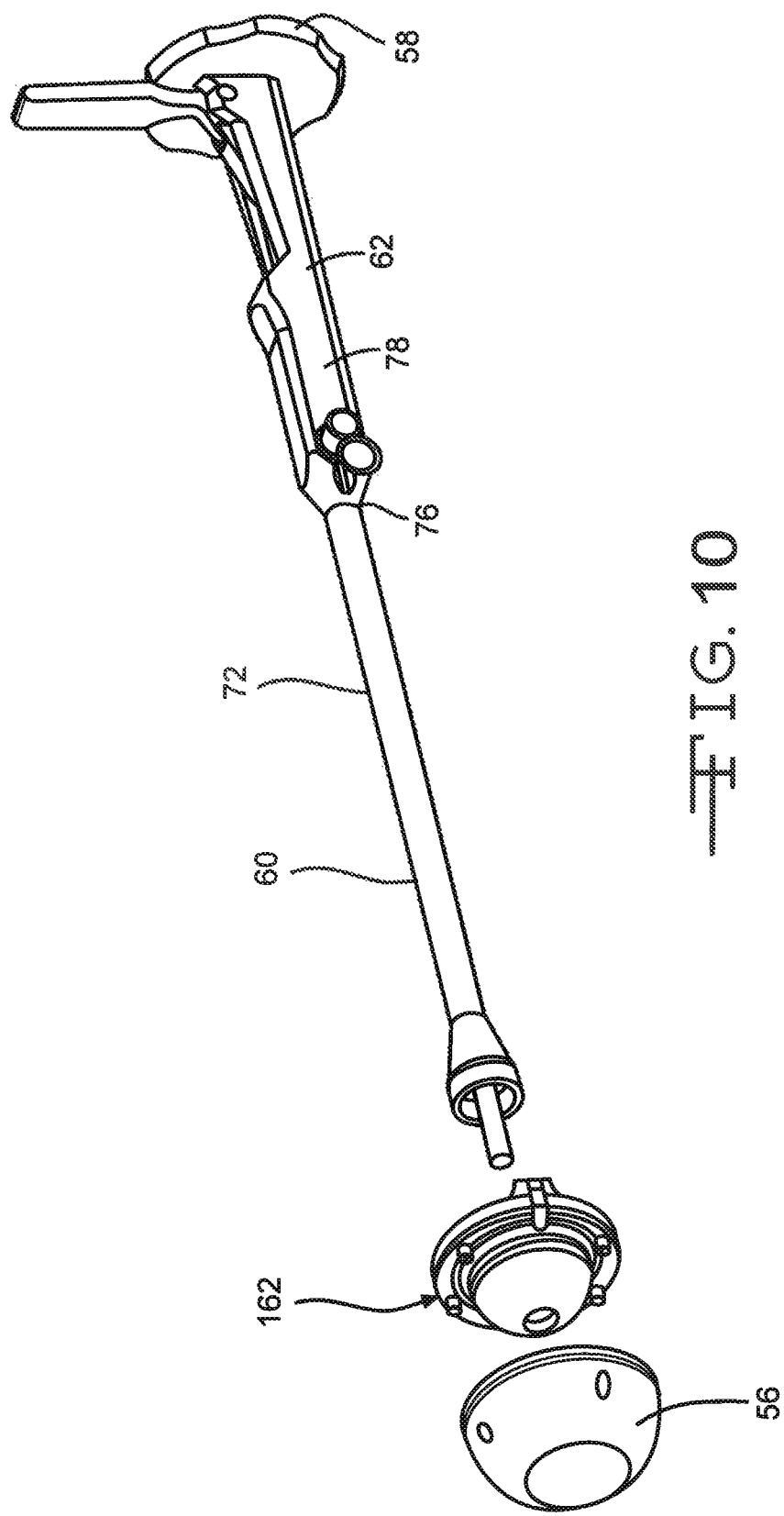
FIG. 10 illustrates an embodiment of an impactor comprising a cup-and-socket type prosthetic engagement mechanism.

Although a threaded screw fitting is the preferred means of attachment of the prosthetic cup 56 to the impactor 50 of the present invention, other cup attachment means could also be used. For example, as illustrated in FIG. 10, a cup-and-socket 162 type mechanism may be used. In addition, the cup attachment mechanism may be adapted for use with a double mobility prosthetic cup utilizing an expandable dome mechanism as disclosed in U.S. patent application Ser. No. 12/694,524, which is assigned to the assignee of the present invention and incorporated herein by reference. Furthermore, a grasping plate cup attachment mechanism as disclosed in U.S. patent application Ser. No. 13/219,767, which is assigned to the assignee of the present invention and incorporated herein by reference, may also be used as well.

Once the prosthetic cup 56 has been securely connected to the distal end of the impactor 50, the impactor and prosthetic cup assembly is inserted within the target area of the acetabulum. Once correctly positioned, a series of impaction forces are delivered to the strike plate 58 to thusly seat the cup 56 in the acetabulum. After the cup 56 is secured within the acetabulum, the impactor 50 is removed from the seated cup. This separation is accomplished by depressing the rocker lever 152 of the ratchet locking mechanism 134. This action raises the distal end portion 142 of the rocker arm 136, disengaging the rocker arm teeth 154 from the teeth 158 of the connection rod 64, thereby enabling the connection rod 64 to move freely within the body and handle portions 60, 62. This rocker arm 136 movement enables the connector rod 64 to extend distally. The strike plate 58 is then rotated in a counter clockwise direction to disengage the prosthetic cup 56 from the connection rod 64 and the body of the impactor is removed from the patient.

Accordingly, the invention is not limited, except by the appended claims.

What is claimed is:

1. An orthopedic impactor, comprising:
   a) an elongated body comprising a body sidewall extending along a longitudinal axis from a body proximal portion having a body proximal end spaced from a body distal portion having a body distal end, wherein the body proximal portion is configured to provide a handle for the impactor;
   b) a through-bore extending longitudinally through the elongate body from the body proximal portion to the body distal end;
   c) a connection rod disposed along the longitudinal axis in the through-bore, wherein the connection rod extends from a connection rod proximal end spaced from a connection rod distal end extending out beyond the body distal end;

d) a linkage comprising a linkage proximal end spaced from a linkage distal end, wherein the linkage distal end is pivotally connected to the connection rod proximal end;

e) a lever arm comprising a lever arm first portion having a lever arm first end spaced from a lever arm second portion, wherein the lever arm first end is pivotally connected to the linkage proximal end at a position along the body that is more proximal than the pivotal connection of the linkage distal end to the connection rod proximal end and wherein the lever arm first portion is pivotally connected to the body proximal portion at a location intermediate the lever arm second portion and the pivotable connection of the lever arm first end to the linkage proximal end; and f) wherein with the lever arm second portion in a first position spaced from both the connection rod and the longitudinal axis, a prosthetic cup is detachably connectable to the connection rod distal end, and g) wherein the lever arm second portion is manipulatable to pivot the lever arm first portion about the pivotable connection on the body proximal portion with the lever arm second portion moving from the first position to a second position spaced closer to both the connection rod and the longitudinal axis than when in the first position to thereby cause the pivotable connection of the lever arm first end to the linkage proximal end to move the linkage proximal end from a third position spaced from the longitudinal axis to a fourth position closer to the longitudinal axis than when in the third position, which movement causes the connection rod to move in a proximal direction within the through-bore in the elongated body with the connection rod distal end moving from a fifth position spaced outwardly from the body distal end to a sixth position spaced closer to the body distal end than when in the fifth position to thereby move the prosthetic cup connected to the connection rod distal end closer to the body distal end, and wherein in the second position, the lever arm first portion is proximal the lever arm second portion.

2. The orthopedic impactor of claim 1 wherein a first pivot pin pivotably connects the connection rod proximal end to the linkage distal end.

3. The orthopedic impactor of claim 1 wherein a second pivot pin pivotably connects the lever arm first end to the linkage proximal end.

4. The orthopedic impactor of claim 1 wherein the body proximal end provides a strike plate.

5. The orthopedic impactor of claim 1 wherein the body distal portion comprises a frusto-conical shape extending distally and outwardly along the longitudinal axis to a threaded cylindrical portion.

6. The orthopedic impactor of claim 5 wherein an end cap is threadingly connectable to the body at the threaded cylindrical portion.

7. The orthopedic impactor of claim 5 wherein the threaded cylindrical portion of the body distal portion is internally threaded.

8. The orthopedic impactor of claim 1 wherein a first opening in open communication with the through-bore extends through the body sidewall of the body proximal portion and wherein at least the linkage and the lever arm first portion moveably reside in the first opening.

9. The orthopedic impactor of claim 8 wherein a third pivot pin pivotably connects the lever arm first portion to opposed supports of the body sidewall at the first cavity of the body proximal portion.

10. The orthopedic impactor of claim 1 wherein the connection rod distal end is threaded to thereby threadingly connect to the prosthetic cup.

11. The orthopedic impactor of claim 1 wherein a ratchet mechanism is mounted to the body sidewall distal where the lever arm is pivotably connected to the linkage and distal where the linkage is pivotably connected to the connection rod.

12. The orthopedic impactor of claim 11 wherein the ratchet mechanism comprises a ratchet housing supported on the body at a second opening extending through the body sidewall and in open communication with the through-bore, and wherein the ratchet housing supports a rocker arm comprising a rocker arm handle spaced from a rocker arm distal portion provided with a plurality of first ratchet teeth that are in a releasable ratchet engagement with a plurality of second ratchet teeth provided on the connection rod to thereby lock the connection rod at a desired position in the through-bore of the body when the first ratchet teeth of the rocker arm are in engagement with the second ratchet teeth on the connection rod.

13. The orthopedic impactor of claim 12 wherein a biasing member biases between the ratchet housing and the rocker arm to thereby maintain the first ratchet teeth of the rocker arm in ratchet engagement with the second ratchet teeth on the connection rod, and wherein pivotable manipulation of the rocker arm handle with respect to the body causes the first teeth to release from their ratchet engagement with the second teeth on the connection rod to thereby provide for axial movement of the connection rod along the through-bore in the body.

14. The orthopedic impactor of claim 11 wherein a fourth pivot pin pivotably connects the rocker arm to the body at the second opening in the body sidewall.

15. An orthopedic impactor, comprising:
a) an elongated body comprising a body sidewall extending along a longitudinal axis from a body proximal portion having a body proximal end spaced from a body distal portion having a body distal end, wherein the body proximal portion is configured to provide a handle for the impactor;

b) a through-bore extending longitudinally through the elongate body from the body proximal portion to the body distal end;

c) a connection rod disposed along the longitudinal axis in the through-bore, wherein the connection rod extends from a connection rod proximal end spaced from a connection rod distal end extending out beyond the body distal end;

d) a linkage comprising a linkage proximal end spaced from a linkage distal end, wherein the linkage distal end is pivotally connected to the connection rod proximal end;

e) a lever arm comprising a lever arm first portion having a lever arm first end spaced from a lever arm second portion, wherein the lever arm first end is pivotally connected to the linkage proximal end and wherein the lever arm first portion is pivotally connected to the body proximal portion at a location intermediate the lever arm second portion and the pivotable connection of the lever arm first end to the linkage proximal end; and f) wherein with the lever arm second portion in a first position spaced from both the connection rod and the longitudinal axis, a prosthetic cup is detachably connectable to the connection rod distal end, and g) wherein the lever arm second portion is manipulatable to pivot the lever arm first portion about the pivotable connection on the body proximal portion with the lever arm second portion moving from the first position to a second position spaced closer to both the connection rod and the longitudinal axis than when in the first position to thereby cause the pivotable connection of the lever arm first end to the linkage proximal end to move the linkage proximal end from a third position spaced from the longitudinal axis to a fourth position with the linkage aligned along the longitudinal axis, which movement causes the connection rod to move in a proximal direction within the through-bore in the elongated body with the connection rod distal end moving from a fifth position spaced outwardly from the body distal end to a sixth position spaced closer to the body distal end than when in the fifth position to thereby move the prosthetic cup connected to the connection rod distal end closer to the body distal end, and wherein in the second position, the lever arm first portion is proximal the lever arm second portion.

16. The orthopedic impactor of claim 15 wherein a first pivot pin pivotably connects the connection rod proximal end to the linkage distal end, a second pivot pin pivotably connects the lever arm first end to the linkage proximal end, and a third pivot pin pivotably connects the lever arm first portion to opposed supports of the body sidewall at the first cavity of the body proximal portion.

17. The orthopedic impactor of claim 15 wherein the body distal portion comprises a frusto-conical shape extending distally and outwardly along the longitudinal axis to a threaded cylindrical portion, and wherein an end cap is threadingly connectable to the body at the threaded cylindrical portion.

18. The orthopedic impactor of claim 15 wherein a first opening in open communication with the through-bore extends through the body sidewall of the body proximal portion and wherein at least the linkage and the lever arm first portion moveably reside in the first opening.

19. The orthopedic impactor of claim 15 wherein the connection rod distal end is threaded to thereby threadingly connect to the prosthetic cup.

20. The orthopedic impactor of claim 15 wherein a ratchet mechanism is mounted to the body sidewall distal where the lever arm is pivotably connected to the linkage and distal where the linkage is pivotably connected to the connection rod, wherein the ratchet mechanism comprises a ratchet housing supported on the body at a second opening extending through the body sidewall and in open communication with the through-bore, and wherein the ratchet housing supports a rocker arm comprising a rocker arm handle spaced from a rocker arm distal portion provided with a plurality of first ratchet teeth that are in a releasable ratchet engagement with a plurality of second ratchet teeth provided on the connection rod to thereby lock the connection rod at a desired position in the through-bore of the body when the first ratchet teeth of the rocker arm are in engagement with the second ratchet teeth on the connection rod, and wherein a biasing member biases between the ratchet housing and the rocker arm to thereby maintain the first ratchet teeth of the rocker arm in ratchet engagement with the second ratchet teeth on the connection rod, and wherein pivotable manipulation of the rocker arm handle with respect to the body causes the first teeth to release from their ratchet engagement with the second teeth on the connection rod to thereby provide for axial movement of the connection rod along the through-bore in the body.

21. An orthopedic impactor, comprising:
a) an elongated body comprising a body sidewall having a first body length extending along a longitudinal axis from a body proximal portion having a body proximal end spaced from a body distal portion having a body distal end, wherein the body proximal portion is configured to provide a handle for the impactor;
b) a through-bore extending longitudinally through the elongate body from the body proximal portion to the body distal end, wherein the through-bore has a second length that is less than the first length of the body;
c) a connection rod disposed along the longitudinal axis in the through-bore, wherein the connection rod extends from a connection rod proximal end spaced from a connection rod distal end extending out beyond the body distal end;
d) a linkage comprising a linkage proximal end spaced from a linkage distal end, wherein the linkage distal end is pivotally connected to the connection rod proximal end;
e) a lever arm comprising a lever arm first portion having a lever arm first end spaced from a lever arm second portion, wherein the lever arm first end is pivotally connected to the linkage proximal end at a position along the body that is more proximal than the pivotal connection of the linkage distal end to the connection rod proximal end and wherein the lever arm first portion is pivotally connected to the body proximal portion at a location intermediate the lever arm second portion and the pivotable connection of the lever arm first end to the linkage proximal end; and
f) wherein with the lever arm second portion in a first position spaced from both the connection rod and the longitudinal axis, a prosthetic cup is detachably connectable to the connection rod distal end, and
g) wherein the lever arm second portion is manipulatable to pivot the lever arm first portion about the pivotable connection on the body proximal portion with the lever arm second portion moving from the first position to a second position spaced closer to both the connection rod and the longitudinal axis than when in the first position to thereby cause the pivotable connection of the lever arm first end to the linkage proximal end to move the linkage proximal end from a third position spaced from the longitudinal axis to a fourth position closer to the longitudinal axis than when in the third position, which movement causes the connection rod to move in a proximal direction within the through-bore in the elongated body with the connection rod distal end moving from a fifth position spaced outwardly from the body distal end to a sixth position spaced closer to the body distal end than when in the fifth position to thereby move the prosthetic cup connected to the connection rod distal end closer the body distal end, and wherein in the second position, the lever arm first portion is proximal the lever arm second portion.

* * * * *